United States Patent [19]

Gyulai et al.

[11] Patent Number: 5,312,588
[45] Date of Patent: May 17, 1994

[54] HYDROGEN PEROXIDE DESTROYING COMPOSITIONS AND METHODS OF MAKING AND USING SAME

[75] Inventors: Peter Gyulai, Santa Ana; Larry K. Thomas, Fullerton, both of Calif.; Hermann Osterwald, Bovenden-Eddigehausen, Fed. Rep. of Germany

[73] Assignee: Allergan, Inc., Irvine, Calif.

[21] Appl. No.: 788,340

[22] Filed: Nov. 6, 1991

Related U.S. Application Data

[62] Division of Ser. No. 485,584, Feb. 27, 1990, abandoned.

[51] Int. Cl.$^5$ .............................. A61L 9/00
[52] U.S. Cl. ............................ 422/30; 424/94.4; 424/94.1; 424/406; 424/409
[58] Field of Search ............... 422/30; 424/409, 464, 424/465, 94.1, 94.4, 468, 475; 514/839, 840; 252/186.25

[56] References Cited

U.S. PATENT DOCUMENTS

| Re. 32,672 | 5/1988 | Huth et al. ........................ 252/95 |
|---|---|---|
| 3,910,296 | 10/1975 | Karageozian et al. ............ 134/2 |
| 3,912,451 | 10/1975 | Gaglia, Jr. ........................ 422/30 |
| 4,499,077 | 2/1985 | Stockel et al. ................... 424/661 |
| 4,557,925 | 12/1985 | Lindahl et al. .................. 424/482 |
| 4,568,517 | 2/1986 | Kaspar et al. .................... 422/30 |
| 4,654,208 | 3/1987 | Stockel et al. ................... 424/78 |
| 4,731,197 | 3/1988 | Eckstein et al. ............. 252/186.27 |
| 4,767,559 | 8/1988 | Kruse et al. .................... 252/106 |
| 4,976,921 | 12/1990 | Itagaki et al. .................. 422/30 |
| 5,145,644 | 9/1992 | Park et al. ...................... 422/30 |

FOREIGN PATENT DOCUMENTS

| 0082798 | 6/1983 | European Pat. Off. . |
|---|---|---|
| 0147100 | 3/1985 | European Pat. Off. . |
| 0209071 | 1/1987 | European Pat. Off. . |
| 0255041A1 | 5/1988 | European Pat. Off. . |
| 0278224 | 8/1988 | European Pat. Off. . |
| 0426489A2 | 8/1991 | European Pat. Off. . |
| 3626082A1 | 11/1988 | Fed. Rep. of Germany . |
| WO86/05695 | 10/1986 | PCT Int'l Appl. . |
| WO90/11786 | 10/1990 | PCT Int'l Appl. . |
| WO91/12826 | 9/1991 | PCT Int'l Appl. . |
| 2139260A | 5/1984 | United Kingdom . |
| 2151039A | 12/1984 | United Kingdom . |
| 2173017A | 3/1986 | United Kingdom . |

OTHER PUBLICATIONS

Chemical Selects Abstract.
Controlled Release Technology Issue 2, 1987.
Eudragit L Data Sheet.

*Primary Examiner*—Richard D. Lovering
*Assistant Examiner*—Joseph D. Anthony
*Attorney, Agent, or Firm*—Frank J. Uxa

[57] ABSTRACT

A composition and methods useful for making such compositions and for using such compositions to destroy hydrogen peroxide in a liquid aqueous medium, such as that used to disinfect contact lenses, are disclosed. The composition comprises a coated core containing at least one hydrogen peroxide destroying component effective when released into a liquid aqueous medium to destroy or cause the destruction of hydrogen peroxide present in the liquid aqueous medium, and a barrier coating acting to substantially prevent the release of the hydrogen peroxide destroying component for a period of time after the composition is initially contacted with a hydrogen peroxide-containing liquid aqueous medium. The barrier coating is substantially water soluble, preferably includes polyvinylpyrrolidone and is applied as a substantially dry, solid material.

7 Claims, No Drawings

HYDROGEN PEROXIDE DESTROYING COMPOSITIONS AND METHODS OF MAKING AND USING SAME

This application is a division of application Ser. No. 485,584, filed Feb. 27, 1990 now abandoned.

BACKGROUND OF THE INVENTION

This invention relates to hydrogen peroxide destroying compositions, and the use of same, to decrease the concentration of, or even substantially eliminate, hydrogen peroxide present in a liquid medium. More particularly, the invention relates to such compositions which are useful in destroying residual hydrogen peroxide present in a liquid aqueous medium containing a contact lens which has been disinfected by the action of hydrogen peroxide.

Contact lenses should be periodically cleaned and disinfected by the user to prevent infection or other deleterious effects on ocular health which may be associated with contact lens wear. Currently, there are several different conventional systems and methods which enable the user to clean and disinfect their contact lenses between wearing times. These conventional cleaning and disinfection systems can be divided into "hot" and "cold" systems. Hot systems require the use of heat to disinfect the contact lenses, whereas cold systems use chemical disinfectants at ambient temperatures to disinfect the lenses.

Within the realm of cold disinfection systems are hydrogen peroxide disinfection systems. Disinfecting hydrogen peroxide solutions are effective to kill the bacteria and fungi which may contaminate contact lenses. However, residual hydrogen peroxide on a disinfected contact lens may cause irritation, burning or trauma to the eye unless this hydrogen peroxide is destroyed, i.e., decomposed, neutralized, inactivated or chemically reduced. Therefore, the destruction of the residual hydrogen peroxide in the liquid medium containing the disinfected contact lens is needed to enable safe and comfortable wear of the disinfected contact lens.

Associated with the problem of hydrogen peroxide destruction in contact lens disinfection systems are the problems of easy use and user compliance. To enhance user compliance and ease of use, several efforts have focused on one-step disinfection and hydrogen peroxide destruction. In this regard, various time release tablets containing a core tablet and a totally soluble or insoluble coating have been suggested.

Kruse et al U.S. Pat. No. 4,767,559 discloses a one-step contact lens cleaning and disinfecting tablet designed to be totally dissolved in water. A core containing a hydrogen peroxide reducing agent and a catalyst is provided. Preferably but not essentially, a thin lacquer polymeric coating, e.g., of acrylic resin or polyvinylpyrrolidone, may be sprayed on the core tablet to form an enveloped core tablet. A non-polymeric jacket mixture containing a hydrogen peroxide generating component is dry coated into the enveloped core tablet. In this case, the jacket mixture dissolves to form hydrogen peroxide to disinfect the contact lens. Subsequently, the thin lacquer polymeric coating enveloping the core tablet is dissolved, resulting in the release of the reducing agent and catalyst. Spraying the thin lacquer polymeric coating on as a liquid mixture, e.g., aqueous solution, can be disadvantageous. For example, the liquid in the mixture may require additional time to evaporate or may not entirely evaporate. This prolongs the tablet production process. In addition, if polyvinylpyrrolidone-containing liquid is sprayed on the core tablet to form the thin lacquer polymeric coating, the coated tablets tend to stick together, thus making further processing more difficult. Further, using a liquid mixture can result in an uneven, or even discontinuous, coating of the core tablet. Also, using liquid solutions of certain polymers is not effective to provide a coating of sufficient thickness to act as a practical delayed release coating.

Schafer et al European Patent Application 86-109,361.5 discloses a hydrogen peroxide neutralizer tablet covered with a water-soluble coating to delay the dissolution of the tablet. The coating is applied by conventional procedures such as by spraying on a film in coating pans, by fluidized bed methods, or in closed systems. This publication does not suggest that the delayed release coating be applied as anything but a liquid. Also, polyvinylpyrrolidone is described as a component of the neutralizer tablet, but not as a component of the coating.

There continues to be a need for a one step contact lens disinfecting system using a hydrogen peroxide destroying component. Tablets which include such components should not stick together during manufacture or storage. Also, the delayed release coating should be of sufficient thickness to allow enough time for lens disinfecting to take place while, at the same time allowing release of the hydrogen peroxide destroying component in a reasonable period of time so that the disinfected lens can be safely and comfortably worn.

SUMMARY OF THE INVENTION

New compositions, methods for making such compositions and methods useful for destroying hydrogen peroxide in a liquid aqueous medium, in particular for destroying residual hydrogen peroxide in a liquid aqueous medium containing a disinfected contact lens, have been discovered. The present invention allows the hydrogen peroxide destroying component or components to be initially contacted with the liquid aqueous medium at the same time the contact lens to be disinfected is initially contacted with liquid aqueous medium. For example, the present compositions and the contact lens to be disinfected can be added to the liquid aqueous medium at substantially the same time. This feature greatly reduces the amount of user time and care required to effectively disinfect his/her lenses and destroy the residual hydrogen peroxide. Better user compliance and a greater degree of user eye safety is provided. The present invention provides a delayed release feature so that the contact lens is effectively disinfected by the action of hydrogen peroxide prior to the release of the hydrogen peroxide destroying component. Also, the present composition is structured so as to provide for rapid release of the hydrogen peroxide destroying agent into the medium. This rapid release feature provides for rapid destruction of the residual hydrogen peroxide after a delayed release of the peroxide destroying component. Thus, the overall time required to both disinfect the lens and destroy the residual peroxide is reduced, thus making contact lens disinfecting more convenient and easy to practice. Further, in certain particularly useful embodiments, the coating used to provide the delayed release feature includes one or more materials which, when dissolved in a liquid aqueous medium, provide one or more benefits to the contact lens or to the wearer of the contact lens.

In one broad aspect, the present invention is directed to a composition including a coated portion, e.g., coated core tablet, containing at least one hydrogen peroxide destroying component, and a barrier coating. The hydrogen peroxide destroying component, hereinafter referred to as HPDC, is effective when released into a liquid aqueous medium to destroy or cause the destruction of hydrogen peroxide present in the liquid aqueous medium. The barrier coating acts to substantially prevent the release of the HPDC for a period of time after the composition is initially contacted with a hydrogen peroxide-containing liquid aqueous medium, hereinafter referred to as HPLM. The barrier coating is preferably substantially water soluble. At least one component of the barrier coating, preferably the entire barrier coating, is applied to the coated portion as a substantially dry, solid material. The barrier coating preferably includes at least one polymeric material. Compositions in which the barrier coating is applied in this manner have been found to have very effective delayed release properties. Thus, the chemical make-up of the barrier coating can be very precisely controlled. Also, the amount, e.g., thickness, of the barrier coating on the coated portion can be very precisely controlled. The ability to control these two parameters provides the present compositions with very effective and controlled delayed release properties. In addition, some materials, in particular polyvinylpyrrolidone, which are useful in the present barrier coatings have previously been ineffective as delayed release coatings due to the inability of placing a sufficient amount of such material on an item to be coated using other methods, e.g., using a liquid sprayed on the item to be coated.

A method for producing the present compositions comprises forming a core, preferably a core tablet, containing at least one HPDC effective when released into a HPLM to destroy or cause the destruction of hydrogen peroxide present in the HPLM; placing the core in a cavity partially filled with substantially dry, solid material; adding an additional amount of this substantially dry, solid material to the cavity; and applying a compressive force to the contents of the cavity to secure the substantially dry, solid material to the core. The coated core, preferably the coated core tablet, thus formed includes a sufficient amount of the substantially dry material to delay the release of the HPDC for a period of time after the coated core is initially contacted, e.g. submerged in, a HPLM. Preferably, at least a portion, more preferably substantially all, of the substantially dry solid is water soluble.

A method for decreasing the concentration of hydrogen peroxide in a HPLM is provided in which a HPLM is contacted with a composition, e.g., as described herein.

Further, a method of disinfecting a lens, preferably a contact lens, is provided. This method includes contacting a lens to be disinfected with a HPLM at effective lens disinfecting conditions to disinfect the lens. The HPLM is also contacted with a composition, e.g., as described herein. This composition preferably produces a liquid aqueous medium having no deleterious concentration of hydrogen peroxide. Thus, after the composition has acted, the disinfected contact lens can be removed from the liquid aqueous medium and placed directly in the eye.

DETAILED DESCRIPTION OF THE INVENTION

The present invention is of value where hydrogen peroxide is used to disinfect all types of lenses, e.g., contact lenses, which are benefited by periodical disinfecting. Such lenses, e.g., conventional contact lenses, in particular soft contact lenses, may be made of any suitable material or combination of materials and may have any suitable configuration not substantially deleteriously affected by hydrogen peroxide, the present compositions or the present methods.

The present invention is particularly useful for destroying residual hydrogen peroxide in a HPLM which has been used to disinfect a contact lens.

The liquid medium used to disinfect a contact lens in the present invention includes a disinfecting amount of hydrogen peroxide. Preferably, a disinfecting amount of hydrogen peroxide means such amount as will reduce the microbial burden by one log in three hours. Still more preferably, the hydrogen peroxide concentration is such that the microbial load is reduced by one log order in one hour. Particularly preferred are those hydrogen peroxide concentrations which reduce the microbial load by one log unit in 10 minutes or less. Relatively mild aqueous hydrogen peroxide solutions, preferably containing about 0.5% to about 6% of hydrogen peroxide (w/v), are known to be effective disinfecting solutions for contact lenses. These solutions are effective at killing bacteria and fungi which may be found on contact lenses. However, once contact lens has been disinfected by being immersed in the HPLM, the residual hydrogen peroxide, e.g., on the lens, should be destroyed so that the lens may be safely and comfortably worn on the eye. If this residua hydrogen peroxide is not destroyed before the lens is worn, irritation to the eye or wearing discomfort may occur.

Thus, the present compositions, which are preferably initially contacted with the HPLM at substantially the same time as the contact lens to be disinfected, allow for effective lens disinfection and, in addition, effectively destroy the residual hydrogen peroxide remaining in the HPLM so that the disinfected lens can be removed from the liquid medium and placed directly into the eye for safe and comfortable wear. The present composition is preferably present in the form of a tablet. The composition may be present in the form of at least one item, e.g., tablet, which includes a coated portion, e.g., a core such as a core tablet, and a barrier coating. The barrier coating preferably substantially surrounds the coated portion, which includes the HPDC. The coated portion is preferably about 40% to about 95% by weight of the total composition, while the barrier coating is preferably about 1% to about 60% by weight of the total composition.

Any suitable HPDC may be included in the present compositions. Such HPDCs should effectively destroy the residual hydrogen peroxide and have no undue detrimental effect on the disinfected lens or on the eye into which the disinfected lens is placed. Among the useful HPDCs are hydrogen peroxide reducing agents, peroxidases (meaning to include therein catalase) and mixtures thereof.

Examples of the hydrogen peroxide reducing agents which are useful in the present invention are alkali metal in particular sodium, thiosulfates; thiourea; alkali metal, in particular sodium, sulfites; thioglycerol; N-acetylcysteine alkali metal, in particular sodium, formiates; ascorbic acid; isoascorbic acid; glyoxylic acid; mixtures thereof and the like. A particularly useful peroxidase is catalase. The peroxidases, and especially catalase, are very beneficial in the present invention since such HPDCs are effective to substantially eliminate hydrogen peroxide from a liquid medium in a reasonable period of time, e.g., on the order of about 1 minute to about 12 hours, preferably about 5 minutes to about 1 hour, after the HPDC is initially released into the HPLM. One important advantage of the present invention is the rapidity with which the HPDC acts to destroy residual hydrogen peroxide once the HPDC is initially released into the HPLM. The present barrier coating can be very precisely formulated and applied so that the amount of time after the composition is introduced into the HPLM but before any HPDC is released into the HPLM is very effectively controlled. After this period of time, the barrier coating is dissolved into the HPLM sufficiently to rapidly release sufficient HPDC to destroy substantially all the remaining or residual hydrogen peroxide. The present compositions are preferably formulated and structured to provide for delayed release of the HPDC into the HPLM for a time sufficient to effectively disinfect a contact lens and then release the HPDC into the HPLM for rapid and predictable destruction of the residual hydrogen peroxide.

The amount of HPDC employed is preferably sufficient to destroy all the hydrogen peroxide present in the HPLM into which the HPDC is placed. Excess HPDC may be employed. Very large excesses of HPDC are to be avoided since the HPDC itself may cause problems with the disinfected contact lens and/or the ability to safely and comfortably wear such disinfected contact lens. When catalase is employed as a HPDC, it is preferably present in an amount of about 100 to about 250, more preferably about 150 to about 200 units of catalase activity/percent (w/v) of hydrogen peroxide in the HPLM/ml of HPLM. For example, an especially useful amount of catalase for use in an aqueous solution containing about 3% (w/v) hydrogen peroxide is about 520 units of catalase activity/ml of solution.

The HPDC may be combined with one or more other components, e.g., in the core of a layered tablet. Such other components may include, for example, fillers, binders, tonicity agents, contact lens conditioning/wetting agents, buffering agents, lubricating agents and the like. Each of these components may be present, if at all, in an amount effective to perform its designated function or functions. Examples of each of these types of components are conventional and well known in the art. Therefore, a detailed description of such components is not presented here. An illustrative HPDC-containing core tablet may have the following composition:

|  | Wt. % |
| --- | --- |
| HPDC | 1–30 |
| Filler | 15–90 |
| Tonicity Agent | 1–90 |
| Buffer | 1–50 |
| Lubricating Agent | 0–30 |

In a particularly useful embodiment, the HPDC is combined with at least one enzyme effective to remove debris from a contact lens. Among the types of debris that form on contact lens during normal use are protein-based debris, mucin-based debris, lipid-based debris and carbohydrate-based debris. One or more types of debris may be present on a single contact lens.

The enzyme employed may be selected from peroxide-active enzymes which are conventionally employed in the enzymatic cleaning of contact lenses. For example, many of the enzymes disclosed in Huth et. al. U.S. Pat. No. RE 32,672 and Karageozian et al U.S. Pat. No. 3,910,296 are useful in the present invention. These patents are incorporated in their entirety by reference herein. Among the useful enzymes are those selected from proteolytic enzymes, lipases and mixtures thereof.

Preferred proteolytic enzymes are those which are substantially free of sulfhydryl groups or disulfide bonds, whose presence may react with the active oxygen in the HPLM to the detriment of the activity of the enzyme. Metalloproteases, those enzymes which contain a divalent metal ion such as calcium, magnesium or zinc bound to the protein, may also be used.

A more preferred group of proteolytic enzymes are the serine proteases, particularly those derived from Bacillus and Streptomyces bacteria and Asperigillus molds. Within this grouping, the still more preferred enzymes are the derived alkaline proteases generically called subtilisin enzymes. Reference is made to Deayl, L., Moser, P. W. and Widi. B. S., "Proteases of the Genus Bacillus. II Alkaline Proteases", Biotechnology and Bioengineering, Vol. XII, pp 213–249 (1970) and Keay, L. and Moser, P. W., "Differentiation of Alkaline Proteases form Bacillus Species" Biochemical and Biophysical Research Comm., Vol 34, No. 5, pp 600–604, (1969).

The subtilisin enzymes are broken down onto two subclasses, subtilisin A and subtilisin B. In the subtilisin A grouping are enzymes derived from such species are *B. subtilis, B. licheniformis* and *B. pumilis*. Organisms in this sub-class produce little or no neutral protease or amylase. The subtilisin B sub-class is made up of enzymes from such organisms a *B. subtilis, B. subtilis var. amylosacchariticus, B. amyloliquefaciens* and *B. subtilis* NRRL B3411. These organisms produce neutral proteases and amylases on a level about comparable to their alkaline protease production. One or more enzymes from the subtilisin A sub-class are particularly useful.

In addition other preferred enzymes are, for example, pancreatin, trypsin, collaginase, keratinase, carboxylase, aminopeptidase, elastase, and aspergillo-peptidase A and B, pronase E (from *S. griseus*) and dispase (from *Bacillus polymyxa*).

An effective amount of enzyme is to be used in the practice of this invention. Such amount will be that amount which effects removal in a reasonable time (for example overnight) of substantially all of at least one type of debris from a lens due to normal wear. This standard is stated with reference to contact lens wearers with a history of normal pattern of lens debris accretion, not the very small group who may at one time or another have a significantly increased rate of debris accretion such that cleaning is recommended every day, or every two or three days.

The amount of enzyme required to make an effective cleaner will depend on several factors, including the inherent activity of the enzyme, and the extent of its interaction with the hydrogen peroxide present.

As a basic yardstick, the working solution should contain sufficient enzyme to provide about 0.001 to about 3 Anson units of activity, preferably about 0.01 to about 1 Anson units, per single lens treatment. Higher or lower amounts may be used.

Enzyme activity is pH dependent so for any given enzyme, there is a particular pH range in which that enzyme will function best. The determination of such range can readily be done by known techniques.

The barrier coating of the present invention is preferably substantially continuous. By "continuous" is meant that the barrier coating completely isolates the coated portion for a time after the present composition is first introduced into, e.g., submerged in, a HPLM. The barrier coating is preferably at least partially water soluble, more preferably substantially complete water soluble.

The barrier coating is applied to the coated portion as a substantially dry, solid material, preferably in the form of a mass of particles or powder. Thus, the barrier coating is applied as a solid, substantially free of an apparent liquid phase. The solid material used to produce the barrier coating may include combined water and/or other normally liquid materials. However, substantially no apparent liquid is present in the solid material when it is applied to the coated portion. The solid material from which the barrier coating is made is preferably compressible. That is, the application of a compressive force, preferably a compressive force such as can be reasonably applied in a conventional tableting operation, is preferably sufficient to cause particles of the solid material to change shape and/or adhere to each other in response to the compressive force.

Any suitable solid material which is capable of functioning as described herein may be employed in the present invention. In certain instances, the solid material when dissolved in the HPLM acts to provide at least one beneficial or desired property to the contact lens or to the wearing of the contact lens. The solid material from which the barrier coating is derived preferably includes at least one polymeric material. Such polymeric material or materials may be present as a major amount of the barrier coating. Examples of solid polymeric materials useful in the present invention include, but are not limited to, polyvinypyrrolidone, polyvinylacetate, polyvinylalcohol, polyacrylates, cellulose ethers and their derivatives, polywaxes and mixtures thereof. A particularly useful soli polymeric material is polyvinylpyrrolidone. A barrier coating including polyvinylpyrrolidone is very effective as a delayed release agent. Moreover, polyvinylpyrrolidone is useful as a contact lens conditioning agent when it is dissolved in the HPLM.

The substantially dry, solid material from which the barrier coating is derived preferably includes at least one lubricant component in an amount effective to facilitate the application of the barrier coating to the coated portion. The lubricant component is preferably about 1% to about 20% by weight of the total barrier coating. Examples of useful lubricant components include, but are not limited to, one or more lubricants conventionally used in tableting operations. A particularly useful lubricant component is selected from the group consisting of polyethylene glycols and mixtures thereof, especially such polyethylene glycols being a molecular weight in the range of about 2,000 to about 10,000. In addition, one or more plasticizers may be employed provided that such plasticizers have substantially no detrimental effect on the contact lens being disinfected or on the wearing of the disinfected contact lens.

An additional embodiment of the present invention provides for a composition in which at least one enzyme capable of removing debris from a contact lens, as described elsewhere herein, is included separate and apart from the HPDC. Preferably, in this embodiment, the composition is present in the form of at least one item, e.g., a tablet, comprising a coated core, a barrier coating and a second coating. The second coating includes the enzyme, and the coated core includes the HPDC. The second coating preferably substantially surrounds the barrier coating, which, preferably, substantially surrounds the coated core. Using this embodiment, the contact lens is preferably cleaned of protein-based debris at the same time the contact lens is disinfected.

The present hydrogen peroxide destroying compositions are preferably prepared as follows. A core, e.g., core tablet, containing at least one HPDC is formed, e.g., using conventional tableting techniques. This core is placed into a cavity partially filled with the substantially dry, solid material, preferably including a polymeric material from which the barrier coating is derived. The cavity preferably contains about 20% to about 80% of the total substantially dry, solid material used to produce a coated core. The cavity is conveniently part of a tablet press coater and is sized and shaped to provide the final composition as a tablet of appropriate size and dimensions. Once the core is in the cavity, an additional amount of the substantially dry, solid material is added to the cavity. A compressive force, e.g., generated in a tablet press coater, is applied to the contents of the cavity. Such application of a compressive force acts to secure the substantially dry, solid material to the core and form a coated core. A sufficient amount of substantially dry, solid material is preferably included in the coated core to delay the release of the HPDC for a period of time, preferably a predetermined period of time, after the coated core is initially contacted with a HPLM.

As noted above, one or more enzymes useful to remove debris from a contact lens can be included with the HPDC or can be located in a second coating. Conventional techniques can be employed to place a second coating containing such enzyme or enzymes on the coated core produced as discussed previously.

The present method of disinfecting a lens, preferably a contact lens, includes contacting the lens to be disinfected with a HPLM at effective lens disinfecting conditions. The HPLM is contacted with a composition which includes a coated portion containing at least one HPDC and a barrier coating, such as described herein. Using this method, the lens is disinfected and the residual hydrogen peroxide in the HPLM is effectively destroyed. Thus, after the HPDC has been released into the HPLM and acts to effectively destroy the residual hydrogen peroxide, the lens can be safely and comfortably taken directly from the liquid medium in which it was disinfected.

In a particularly useful embodiment, the contact lens to be disinfected is placed into the HPLM at substantially the same time as in the present composition. After a predetermined period of time, during which the contact lens is disinfected, the HPDC is released into the HPLM and effectively destroys the residual hydrogen peroxide.

In the event that a protein-based debris removing enzyme is present in the composition, the contact lens in the liquid medium is also effectively cleaned of any protein-based debris. This cleaning action can occur either at the time the lens is being disinfected, e.g., if the enzyme is released into the HPLM when the composition is initially contacted with the HPLM or shortly thereafter; or after the lens is disinfected, e.g., if the enzyme is released into the HPLM when the HPDC is released into the HPLM or thereafter.

It is preferred that the HPDC not be released into the HPLM until the lens has been immersed in the HPLM for a time sufficient, more preferably in the range of about 1 minute to about 4 hours and still more preferably in the range of about 5 minutes to about 1 hour, to effectively disinfect the lens. It is also preferred that substantially all of the residual hydrogen peroxide in the HPLM be destroyed in less than about 3 hours, more preferably in less than about 1 hour and still more preferably in less than about 30 minutes, after the HPDC is initially released into the HPLM.

The disinfecting contacting preferably occurs at a temperature to maintain the liquid medium substantially liquid. For example, when the liquid medium is aqueous-based, it is preferred that the contacting temperature be in the range of about 0° C. to about 100° C., and more preferably in the range of about 10° C. to about 60° C. and still more preferably in the range of about 15° C. to about 30° C. Contacting at or about ambient temperature is very convenient and useful. The contacting preferably occurs at or about atmospheric pressure. This contacting preferably occurs for a time to substantially completely disinfect the lens being treated. Such contacting times can be in the range of about 1 minute to about 12 hours or more.

The following non-limiting examples illustrate certain aspects of the present invention.

EXAMPLE 1

A two layer tablet, having a core tablet surrounded by a coating was prepared for testing. The core tablet and coating had the following compositions:

| CORE TABLET | |
| --- | --- |
| Crystalline catalase[1] | 1.5 mg |
| Sodium chloride | 89.4 mg |
| Dibasic sodium phosphate (anhydrous) | 12.0 mg |
| Monobasic sodium phosphate monohydrate | 1.0 mg |
| Polyethylene glycol (molecular weight of about 3350) | 1.0 mg |
| COATING | |
| Polyvinylpyrrolidone[2] | 90 mg |
| Polyethylene glycol[3] | 9.1 mg |

[1]The amount of catalase added was determined by an assay of the batch of product to be used.
The tablet prepared contained about 5200 units of catalase activity.
[2]Polyvinylpyrrolidone having a weight average molecular weight of about 1,100,00 and sold by BASF under the trademark Kollidon 90.
[3]Polyethylene glycol having a molecular weight of about 3350.

The coating was applied to the core tablet as follows. The coating material was provided in the form of a substantially dry solid powder. A Kilian RUD press coater was employed and was equipped with 7 mm. tooling. About 40-50% of the amount of coating material required for one coated tablet was placed into the cavity of the tool. The core tablet was then placed in the cavity. The remainder of the amount of coating composition required for one coated tablet was then placed in the cavity. The press coater was then operated to apply a compressive force to the contents of this cavity. The resulting layered tablet appeared to have a continuous, substantially uniform outer layer of the coating composition. Further, this layered tablet was not sticky to the touch and did not stick to other layered tablets.

This layered tablet was tested to determine its effectiveness in destroying hydrogen peroxide. This test was conducted as follows. 10 ml of a 3% (w/v) aqueous solution of hydrogen peroxide was provided at room temperature. The layered tablet was introduced into the solution and periodic measurements of the amount of oxygen released from the solution were made. The amount of oxygen released was used to determine the hydrogen peroxide concentration remaining in the solution.

Results of this test were as follows:

| Time After Tablet Introduced Into Solution, min | Peroxide Concentration In Solution, % w/v |
| --- | --- |
| 0 | 3.10 |
| 33.5 | 3.10 |
| 34 | 3.02 |
| 35 | 2.29 |
| 36 | 1.06 |
| 37.5 | 0.34 |
| 39.5 | 0.09 |
| 41.5 | 0.0 |

These results demonstrate that the coating effectively delays the release of the catalase for a time sufficient to allow the action of the hydrogen peroxide in the aqueous solution to effectively disinfect a contact lens which is introduced into the solution at the same time as the two layered tablet is introduced. Further, these results also demonstrate that the hydrogen peroxide in the solution can be substantially completely destroyed by the catalase very quickly and very completely after release of the catalase so that a disinfected contact lens can be removed from this solution and placed directly onto a human eye for safe and comfortable wear.

EXAMPLE 2

A layered tablet in accordance with Example 1 is used to disinfect a conventional soft contact lens as follows. 10 ml of a 3% (w/v) aqueous solution of hydrogen peroxide is provided at room temperature. The contact lens to be disinfected and the layered tablet are placed in the solution at the same time. For approximately one-half hour, the solution remains substantially quiet, i.e., substantially no bubbing (gas evolution) takes pace. For the next approximately 5 to 10 minutes, the solution bubbles. After this period of time, the solution becomes and remains quiet. One hour after the contact lens is first introduced into the solution, it is removed from the solution and placed directly into the wearer's eye. It is found that after one hour, the contact lens is effectively disinfected. Also, the lens wearer experiences no discomfort or eye irritation from wearing the disinfected contact lens. The bubbling of the solution provides a indication that hydrogen peroxide destruction is occurring. An indication that the peroxide destruction is complete is provided when the bubbling stops.

EXAMPLE 3

A layered tablet is prepared as in Example 1 except that sufficient subtilisin A is included in the core tablet to provide the core tablet with about 0.4 mg of this enzyme.

This enzyme containing tablet is used to disinfect and clean a protein-based debris laden soft contact lens as follows. 10 ml of a 3% (w/v) aqueous solution of hydrogen peroxide is provided at room temperature. The contact lens to be disinfected and cleaned and the enzyme-containing layered tablet are placed in the solution at the same time. For approximately one-half hour the solution remains substantially quiet. For the next approximately 5 to 10 minutes, the solution bubbles. After this period of time, the solution becomes and remains quiet. 10 hours after the contact lens is first introduced into the solution, it is removed from the solution, rinsed with physiological saline solution to remove the subtilisin A and placed into the wearer's eye. It is found that after 10 hours, the contact lens is effectively disinfected and cleaned of protein-based debris. The lens wearer experiences no discomfort or eye irritation from wearing the disinfected and cleaned contact lens.

EXAMPLE 4

A layered tablet is prepared as in Example 1, and is further spray coated with an aqueous mixture of polyvinylpyrrolidone, sodium carbonate and subtilisin A. The spray coated tablet is dried. The amount of subtilisin A is sufficient to provide the core tablet with about 0.4 mg of this enzyme selected.

This enzyme-containing tablet is used to disinfect and clean a protein-based debris laden soft contact lens substantially as described in Example 3. 10 hours after the contact lens is first introduced into the solution, it is removed from the solution, rinsed with physiological saline solution to remove the subtilisin A and placed into the wearer's eye. It is found that after 10 hours, the contact lens is effectively disinfected and cleaned of protein-based debris. The lens wearer experiences no discomfort or eye irritation from wearing this disinfected and cleaned contact lens.

While this invention has been described with respect to various specific examples and embodiments, it is to be understood that the invention is not limited thereto and that it can be variously practiced within the scope of the following claims.

What is claimed is:

1. A method for producing a delayed release hydrogen peroxide destroying composition comprising:

forming a core containing at least one hydrogen peroxide destroying component effective when released into a hydrogen peroxide-containing liquid medium to destroy or cause the destruction of hydrogen peroxide present in the hydrogen peroxide-containing liquid medium;

placing said core in a cavity partially filled with solid material, said solid material being substantially free of an apparent liquid phase;

adding an additional amount of said solid material to said cavity; and applying a compressive force to the contents of said cavity, thereby securing said solid material, which acts as a delayed releasing agent for said core material, to said core and forming a coated core.

2. The method of claim 1 wherein a sufficient amount of said solid material is included in said coated core to delay the release of said hydrogen peroxide destroying component for a period of time in the range of about 1 minute to about 4 hours after said coated core is initially contacted with a hydrogen peroxide-containing liquid medium.

3. The method of claim 1 wherein between about 20% to about 80% of the total amount of said solid material included in said cavity is included in said cavity prior to said placing step.

4. The method of claim 1 wherein said core further contains at least one enzyme capable of removing debris from a contact lens.

5. The method of claim 1 wherein said solid material includes at least one polymeric material and at least one lubricant component in an amount effective to facilitate said applying step.

6. The method of claim 5 wherein said polymeric material is selected from the group consisting of polyvinylpyrrolidone, polyvinylacetate, polyvinylalcohol, polyacrylates, cellulose ethers and their derivatives, polywaxes and mixtures thereof.

7. The method of claim 5 wherein said polymeric material is polyvinylpyrrolidone and said lubricant component is polyethylene glycol having a molecular weight in the range of about 2,000 to about 10,000.

* * * * *